US012639817B2

(12) United States Patent
Igarashi et al.

(10) Patent No.: US 12,639,817 B2
(45) Date of Patent: May 26, 2026

(54) ULTRASONOGRAPHY APPARATUS, IMAGE PROCESSING APPARATUS, ULTRASOUND IMAGE CAPTURING METHOD, AND ULTRASOUND IMAGE CAPTURING PROGRAM

(71) Applicant: FUJIFILM Corporation, Tokyo (JP)

(72) Inventors: Riki Igarashi, Kanagawa (JP); Tsuyoshi Matsumoto, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 285 days.

(21) Appl. No.: 18/475,176

(22) Filed: Sep. 26, 2023

(65) Prior Publication Data

US 2024/0112344 A1 Apr. 4, 2024

(30) Foreign Application Priority Data

Sep. 30, 2022 (JP) ................................. 2022-159109

(51) Int. Cl.
*G06T 7/00* (2017.01)
*A61B 8/00* (2006.01)
(Continued)

(52) U.S. Cl.
CPC ............ *G06T 7/0016* (2013.01); *A61B 8/463* (2013.01); *A61B 8/5246* (2013.01); *G06T 7/70* (2017.01);
(Continued)

(58) Field of Classification Search
CPC ..................... G06T 7/0016; G06T 7/70; G06T 2207/10132; G06T 2207/30101;
(Continued)

(56) References Cited

U.S. PATENT DOCUMENTS 12,387,334 B2 * 8/2025 Inoue ..................... A61B 8/463
2014/0316236 A1 10/2014 Umezawa
(Continued)

FOREIGN PATENT DOCUMENTS

JP 2014-209977 A 11/2014
JP 2015-112443 A 6/2015
(Continued)

OTHER PUBLICATIONS

The extended European search report issued by the European Patent Office on Dec. 11, 2023, which corresponds to European Patent Application No. 23200187.5-1126 and is related to U.S. Appl. No. 18/475,176.
(Continued)

*Primary Examiner* — Ross Varndell
*Assistant Examiner* — Rachel L Roberts
(74) *Attorney, Agent, or Firm* — Studebaker Brackett PLLC

(57) ABSTRACT

The ultrasonography apparatus includes at least one processor, in which the processor acquires, from a detector that detects a posture of a palm of a subject in capturing an ultrasound image, information representing a posture of the palm at a first time point as a first detection result, acquires information representing a posture of the palm at a second time point, which is after the first time point and is a time point during capturing of the ultrasound image, as a second detection result, derives a difference between the posture of the palm at the first time point and the posture of the palm at the second time point based on the first detection result and the second detection result, and performs notification in a case in which the derived difference is equal to or greater than a threshold value.

8 Claims, 6 Drawing Sheets

(51) Int. Cl.
*A61B 8/08* (2006.01)
*G06T 7/70* (2017.01)

(52) U.S. Cl.
CPC ... *A61B 8/0891* (2013.01); *G06T 2207/10132* (2013.01); *G06T 2207/30101* (2013.01); *G06T 2207/30168* (2013.01); *G06T 2207/30196* (2013.01)

(58) Field of Classification Search
CPC . G06T 2207/30168; G06T 2207/30196; G06T 7/20; G06T 2207/10016; G06T 7/0012; G06T 2207/30004; A61B 8/463; A61B 8/5246; A61B 8/0891; A61B 8/085; A61B 8/467; A61B 8/469; A61B 8/5223; A61B 8/54; A61B 8/5207
See application file for complete search history.

(56) References Cited

U.S. PATENT DOCUMENTS

2015/0164328 A1 6/2015 Yoshitomi
2020/0022671 A1 1/2020 Noguchi
2022/0019283 A1* 1/2022 Morimoto ............... G06F 3/015
2022/0211347 A1* 7/2022 McLeod .............. A61B 8/5207

FOREIGN PATENT DOCUMENTS

JP 2018-015652 A 2/2018
JP 2019-165836 A 10/2019
WO 2018/181127 A1 10/2018
WO 2022/059539 A1 3/2022

OTHER PUBLICATIONS

McIntosh Jess et al., "EchoFlex: Hand Gesture Recognition using Ultrasound Imaging", Interaction Design and Children, AMC, May 2, 2017, pp. 1923-1934, doi: 10.1145/3025453.3025807.

Wu Wei et al., "Low-cost biometric recognition system based on NIR palm vein image", IET Biometrics, IEEE, vol. 8, No. 3, May 1, 2019, pp. 206-214, doi: 10.1049/iet-bmt.2018.5027.

An Office Action, "Notice of Reasons for Refusal," mailed by the Japanese Patent Office on Feb. 3, 2026, which corresponds to Japanese Patent Application No. 2022-159109 and is related to U.S. Appl. No. 18/475,176; with English language translation.

* cited by examiner

ULTRASONOGRAPHY APPARATUS, IMAGE PROCESSING APPARATUS, ULTRASOUND IMAGE CAPTURING METHOD, AND ULTRASOUND IMAGE CAPTURING PROGRAM

CROSS-REFERENCE TO RELATED APPLICATIONS

This application is based on and claims priority under 35 USC 119 from Japanese Patent Application No. 2022-159109, filed Sep. 30, 2022, the disclosure of which is incorporated herein by reference in their entirety.

TECHNICAL FIELD

The present disclosure relates to an ultrasonography apparatus, an image processing apparatus, an ultrasound image capturing method, and an ultrasound image capturing program.

RELATED ART

An ultrasound diagnostic apparatus that captures an ultrasound image of a subject by using an ultrasound probe that receives an ultrasound echo of an ultrasonic wave transmitted to the subject and outputs a reception signal based on the received ultrasound echo is known.

A technique of determining whether or not a captured ultrasound image is suitable for a medical examination is known. For example, in WO2022/059539A, a technique of acquiring a plurality of ultrasound images of a lung of a subject and determining whether or not the ultrasound image is suitable for a diagnosis is known.

With the technique disclosed in WO2022/059539A, it is possible to determine whether or not the ultrasound image is suitable for a diagnosis of a lung, but it is not possible to determine whether or not the ultrasound image is suitable for a diagnosis of parts other than the lung. For example, with the technique disclosed in WO2022/059539A, it is not possible to determine whether or not the ultrasound image is suitable for a diagnosis of a blood vessel in an arm.

SUMMARY

The present disclosure has been made in view of the above circumstances, and an object of the present disclosure is to provide an ultrasonography apparatus, an image processing apparatus, an ultrasound image capturing method, and an ultrasound image capturing program capable of obtaining an ultrasound image suitable for a diagnosis.

In order to achieve the above-described object, a first aspect according to the present disclosure provides an ultrasonography apparatus comprising: at least one processor, in which the processor acquires, from a detector that detects a posture of a palm of a subject in capturing an ultrasound image, information representing a posture of the palm at a first time point as a first detection result, acquires information representing a posture of the palm at a second time point, which is after the first time point and is a time point during capturing of the ultrasound image, as a second detection result, derives a difference between the posture of the palm at the first time point and the posture of the palm at the second time point based on the first detection result and the second detection result, and performs notification in a case in which the derived difference is equal to or greater than a threshold value.

A second aspect according to the present disclosure provides the ultrasonography apparatus according to the first aspect, in which the first time point is a start time point of capturing the ultrasound image.

A third aspect according to the present disclosure provides the ultrasonography apparatus according to the first aspect, in which the processor adds information representing a warning to the ultrasound image captured at the second time point in a case in which the derived difference is equal to or greater than the threshold value.

A fourth aspect according to the present disclosure provides an image processing apparatus performing image processing on a plurality of ultrasound images captured by an ultrasonography apparatus that acquires, from a detector that detects a posture of a palm of a subject in capturing an ultrasound image, information representing a posture of the palm at a first time point as a first detection result, acquires information representing a posture of the palm at a second time point, which is after the first time point and is a time point during capturing of the ultrasound image, as a second detection result, derives a difference between the posture of the palm at the first time point and the posture of the palm at the second time point based on the first detection result and the second detection result, and adds information representing a warning to the ultrasound image captured at the second time point in a case in which the derived difference is equal to or greater than a threshold value, the image processing apparatus comprising: at least one processor, in which the processor acquires the plurality of ultrasound images captured by the ultrasonography apparatus, and generates an object-of-interest image from the plurality of ultrasound images.

A fifth aspect according to the present disclosure provides the image processing apparatus according to the fourth aspect, in which, in a case in which the acquired plurality of the ultrasound images include the ultrasound image to which the information representing the warning is added, the processor generates the object-of-interest image from the plurality of ultrasound images excluding the ultrasound image to which the information representing the warning is added.

A sixth aspect according to the present disclosure provides the image processing apparatus according to the fourth aspect, in which the processor displays a region generated from the ultrasound image to which the information representing the warning is added and a region generated from an ultrasound image other than the ultrasound image to which the information representing the warning is added, of the generated object-of-interest image, in an identifiable manner.

A seventh aspect according to the present disclosure provides the image processing apparatus according to the fourth aspect, in which the processor generates the object-of-interest image by making a weighting of the ultrasound image to which the information representing the warning is added different from a weighting of an ultrasound image other than the ultrasound image to which the information representing the warning is added.

In addition, in order to achieve the above-described object, an eighth aspect according to the present disclosure provides an ultrasound image capturing method executed by a processor, the method comprising: acquiring, from a detector that detects a posture of a palm of a subject in capturing an ultrasound image, information representing a posture of the palm at a first time point as a first detection result; acquiring information representing a posture of the palm at a second time point, which is after the first time point and is a time point during capturing of the ultrasound image, as a second detection result; deriving a difference between the posture of the palm at the first time point and the posture of the palm at the second time point based on the first detection result and the second detection result; and performing notification in a case in which the derived difference is equal to or greater than a threshold value.

In addition, in order to achieve the above-described object, a ninth aspect according to the present disclosure provides an ultrasound image capturing program for causing a processor to execute a process comprising: acquiring, from a detector that detects a posture of a palm of a subject in capturing an ultrasound image, information representing a posture of the palm at a first time point as a first detection result; acquiring information representing a posture of the palm at a second time point, which is after the first time point and is a time point during capturing of the ultrasound image, as a second detection result; deriving a difference between the posture of the palm at the first time point and the posture of the palm at the second time point based on the first detection result and the second detection result; and performing notification in a case in which the derived difference is equal to or greater than a threshold value.

According to the present disclosure, it is possible to obtain an ultrasound image suitable for a diagnosis.

DETAILED DESCRIPTION

Hereinafter, an embodiment of the present invention will be described in detail with reference to the drawings. The present embodiment does not limit the present invention.

Figure 1:
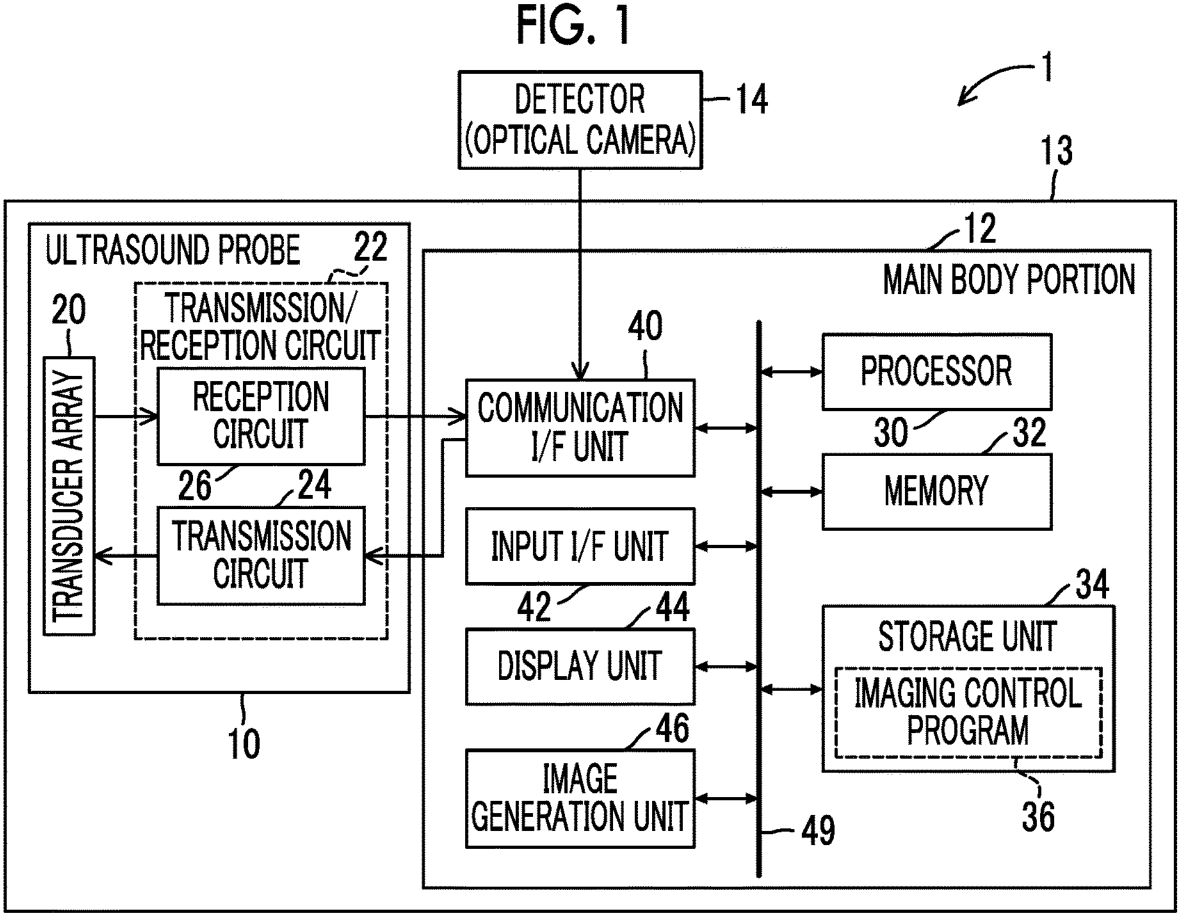
FIG. 1 is a block diagram showing an example of an overall configuration of a medical image capturing system according to an embodiment.

First, an example of an overall configuration of a medical image capturing system 1 according to the present embodiment will be described. FIG. 1 shows a block diagram showing an example of the overall configuration of the medical image capturing system 1 according to the present embodiment. As shown in FIG. 1, the medical image capturing system 1 according to the present embodiment comprises an ultrasonography apparatus 13 and a detector 14.

As shown in FIG. 1, the ultrasonography apparatus 13 according to the present embodiment comprises an ultrasound probe 10 and a main body portion 12.

The ultrasound probe 10 comprises a transducer array 20 and a transmission/reception circuit 22 including a transmission circuit 24 and a reception circuit 26. The transducer array 20 comprises a plurality of transducers (not shown) arranged in a one-dimensional or two-dimensional manner. As an example, in the present embodiment, an aspect in which the ultrasound probe 10 is a linear-type ultrasound probe in which a plurality of transducers are linearly arranged will be described. The ultrasound probe 10 is not limited to this aspect, and may be a convex-type or sector-type ultrasound probe in which the transducers are arranged in a curved manner. Each of the plurality of transducers transmits an ultrasonic wave based on a drive signal applied from the transmission circuit 24, receives an ultrasound echo generated in a subject, and outputs an electric signal in response to the received ultrasound echo.

Each of the plurality of transducer is configured by forming electrodes at both ends of a piezoelectric body which is a piezoelectric material, such as piezoelectric ceramic represented by lead zirconate titanate (PZT), a polymeric piezoelectric element represented by poly vinylidene di fluoride (PVDF), and piezoelectric single crystal represented by lead magnesium niobate-lead titanate (PMN-PT).

The transmission circuit 24 causes the transducer array 20 to transmit an ultrasound beam toward the subject. Specifically, the transmission circuit 24 includes, for example, a plurality of pulse generators (not shown), and, based on a transmission delay pattern selected in response to a control signal from an imaging controller 90 of the main body portion 12, each delay amount is adjusted to supply the drive signal and apply a voltage to each of the plurality of transducers included in the transducer array 20. Each drive signal is a pulse-like or continuous wave-like voltage signal, and in a case in which a voltage is applied to the electrodes of the transducers of the transducer array 20, the piezoelectric body expands and contracts. As a result of the expansion and contraction, pulsed or continuous ultrasonic waves are generated from each transducer, and an ultrasound beam is formed from a combined wave of these ultrasonic waves.

The transmitted ultrasound beam is reflected by each part (for example, a blood vessel or other tissue) in the subject, an instrument disposed in the subject, or the like, thereby generating an ultrasound echo. The generated ultrasound echo propagates in the subject and is received by the plurality of transducers included in the transducer array 20. Each transducer generates an electric signal corresponding to the received ultrasound echo. The electric signal generated in each transducer is output to the reception circuit 26.

Figure 2:
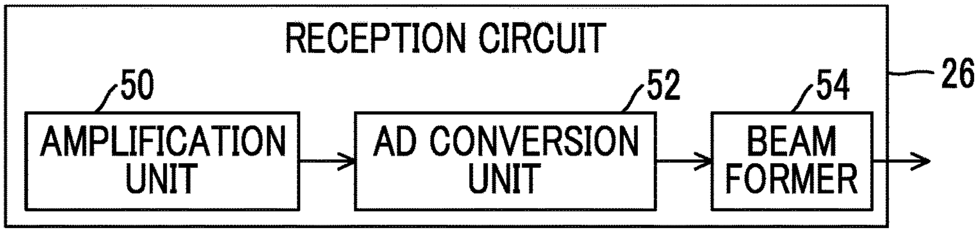
FIG. 2 is a block diagram showing an example of a configuration of a reception circuit.

The reception circuit 26 generates a sound ray signal by performing processing on a signal (strictly speaking, an analog electric signal) output from the transducer array 20 in accordance with the control signal from the imaging controller 90 of the main body portion 12. FIG. 2 is a block diagram showing an example of a configuration of the reception circuit 26 according to the present embodiment. As shown in FIG. 2, the reception circuit 26 includes, for example, an amplification unit 50, an analog digital (AD) conversion unit 52, and a beam former 54.

The amplification unit 50 amplifies the electric signal output from each of the plurality of transducers included in the transducer array 20, and outputs the amplified electric signal to the AD conversion unit 52. The AD conversion unit 52 converts the amplified electric signal into digital reception data, and outputs each piece of the converted reception data to the beam former 54. The beam former 54 performs reception focus processing by giving and adding delay with respect to each piece of the reception data converted by the AD conversion unit 52, in accordance with a sound velocity or a sound velocity distribution set based on a reception delay pattern selected in response to the control signal from the imaging controller 90 of the main body portion 12. Through the reception focusing processing, a sound ray signal in which each piece of the reception data converted by the AD conversion unit 52 is phased and added and the focus of the ultrasound echo is narrowed is generated. The generated sound ray signal is output to the image generation unit 46 via a communication interface (UF) unit 40 of the main body portion 12.

On the other hand, the main body portion 12 comprises a processor 30, a memory 32, a storage unit 34, the communication I/F unit 40, an input I/F unit 42, a display unit 44, and the image generation unit 46. The processor 30, the memory 32, the storage unit 34, the communication I/F unit 40, the input I/F unit 42, the display unit 44, and the image generation unit 46 are connected to each other via a bus 49 such as a system bus or a control bus such that various kinds of information can be exchanged.

The processor 30 reads out various programs, which include an imaging control program 36 stored in the storage unit 34, to the memory 32 and executes processing according to the read-out program. Accordingly, the processor 30 controls capturing of an ultrasound image, and image processing on the ultrasound image. The memory 32 is a work memory that is used for the processor 30 to execute processing.

The storage unit 34 stores image data of the ultrasound image generated by the image generation unit 46, posture information P acquired from the detector 14, the imaging control program 36, marker feature information 38 to be described in detail below, and various other kinds of information. Specific examples of the storage unit 34 include a hard disk drive (HDD), a solid state drive (SSD), and a secure digital (SD) card.

The communication I/F unit 40 performs communication of various kinds of information with an external device of the ultrasound probe 10, the detector 14, and the main body portion 12 through wireless communication such as WiFi (registered trademark) or Bluetooth (registered trademark) or wired communication. A control signal for capturing the ultrasound image is output from the main body portion 12 to the ultrasound probe 10 via the communication I/F unit 40. In addition, a sound ray signal is input from the ultrasound probe 10 to the main body portion 12 via the communication I/F unit 40. In addition, the posture information P is input from the detector 14 to the main body portion 12 via the communication I/F unit 40.

The input I/F unit 42 and the display unit 44 function as a user interface. The display unit 44 provides a user with various kinds of information regarding the capturing of the ultrasound image. The display unit 44 is not particularly limited, and examples of the display unit 44 include a liquid crystal monitor and a light emitting diode (LED) monitor. In addition, the input I/F unit 42 is operated by the user in order to input various instructions regarding the capturing of the ultrasound image or the like. The input I/F unit 42 is not particularly limited, and examples of the input OF unit 42 include a keyboard, a touch pen, and a mouse. A touch panel display in which the input OF unit 42 and the display unit 44 are integrated may be adopted.

Figure 3:
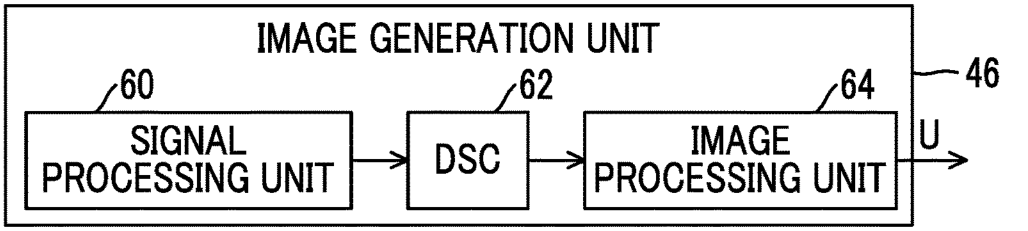
FIG. 3 is a block diagram showing an example of a configuration of an image generation unit.

The image generation unit 46 has a function of generating the ultrasound image based on the sound ray signal input from the reception circuit 26 of the ultrasound probe 10. FIG. 3 shows a block diagram showing an example of a configuration of the image generation unit 46 according to the present embodiment. As shown in FIG. 3, the image generation unit 46 includes, for example, a signal processing unit 60, a digital scan converter (DSC) 62, and an image processing unit 64. The signal processing unit 60 generates a B-mode image signal representing an ultrasound image U by performing, on the sound ray signal generated by the reception circuit 26, attenuation correction due to a distance according to a depth of a reflection position of the ultrasonic wave and then performing envelope detection processing. The DSC 62 converts the B-mode image signal generated by the signal processing unit 60 into an image signal according to a normal television signal scanning method by raster conversion or the like. The image processing unit 64 performs required various image processing such as gradation processing on the B-mode image signal input from the DSC 62, and then outputs the B-mode image signal. The B-mode image signal output from the image generation unit 46 corresponds to the ultrasound image U.

Figure 4:
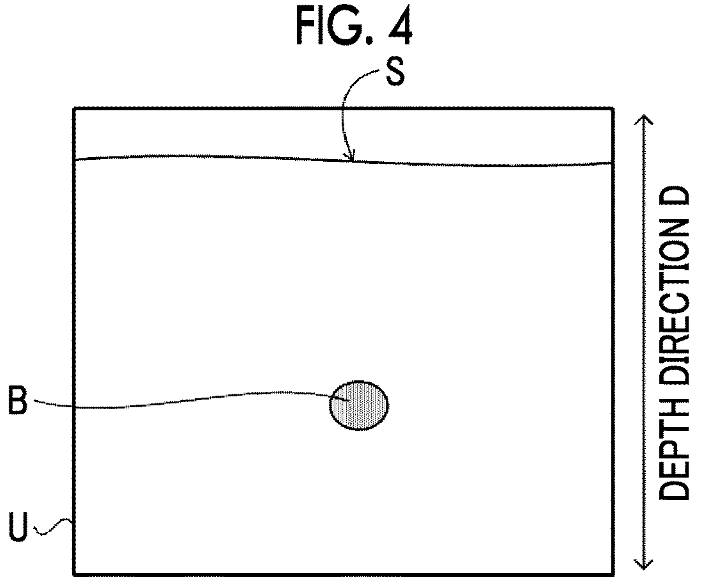
FIG. 4 is a diagram showing an example of an ultrasound image.

FIG. 4 shows an example of the ultrasound image U generated by the image generation unit 46. The ultrasound image U shown in FIG. 4 shows a cross section of a blood vessel B. Here, the cross section of the blood vessel B means a cut surface orthogonal to an extension direction of the blood vessel B. In the present embodiment, as shown in FIG. 4, in the ultrasound image U, each portion of the blood vessel B in the ultrasound image U, in which a direction connecting a body surface S and an inside of the subject is called a depth direction D, is displayed in the depth direction D at a position corresponding to a distance from the body surface S of the subject with which the ultrasound probe 10 is in contact, that is, a depth.

Figure 5:
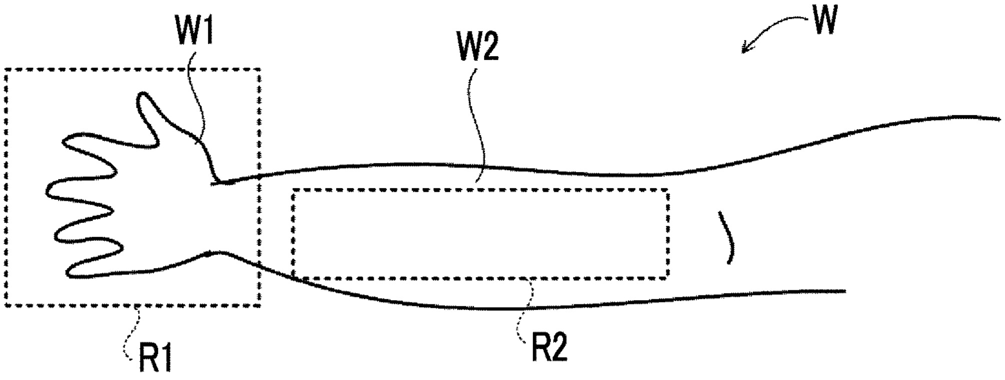
FIG. 5 is a diagram for describing a method of detecting posture information by a detector.

On the other hand, the detector 14 is a detector that detects a posture of a palm of the subject. In the present embodiment, as shown in FIG. 5, as the detector 14, an optical camera in which a region including a palm W1 of a subject W is set as an imaging range R1 is used as a sensor for detecting the posture information P. Therefore, an optical camera image captured by the optical camera of the detector 14 is an image corresponding to the imaging range R1. An imaging range of the ultrasound image U in the present embodiment is an imaging range R2 shown in FIG. 5, and the ultrasound image U is captured with an arm W2 of the subject W as an imaging part.

In a case in which a detection start instruction is input from the main body portion 12 of the ultrasonography apparatus 13, the optical camera of the detector 14 according to the present embodiment continuously captures optical camera images at a set frame rate until a detection end instruction is input from the main body portion 12. The detector 14 estimates the posture information P of the palm W1 using the optical camera image of each frame as a sensor value, and sequentially outputs the estimated posture information P to the ultrasonography apparatus 13.

Figure 6:
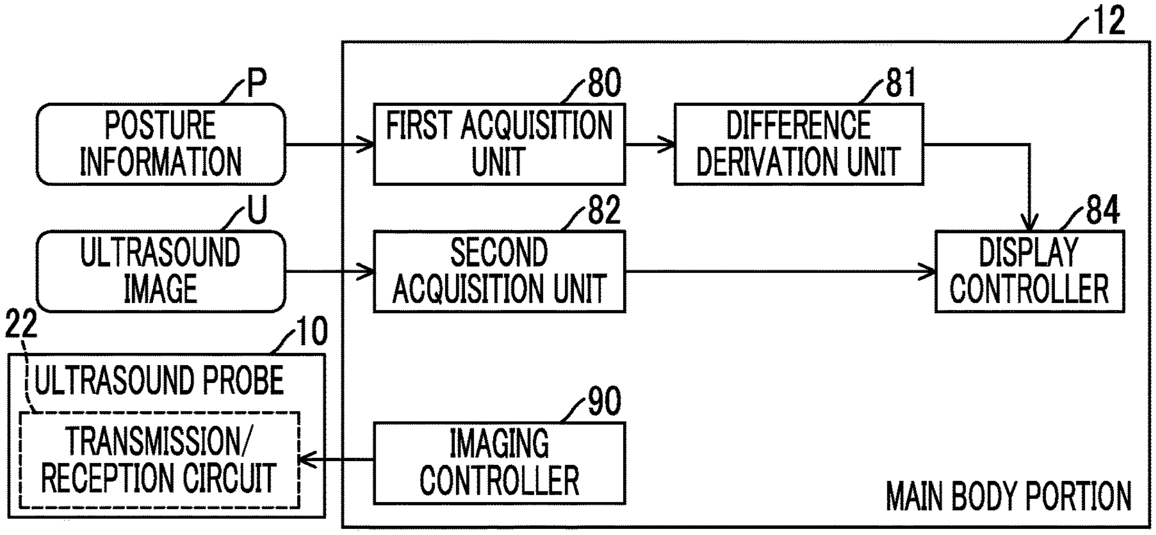
FIG. 6 is a functional block diagram showing an example of a configuration of a main body portion in an ultrasound image.

Next, a functional configuration of the main body portion 12 of the ultrasonography apparatus 13 will be described. FIG. 6 shows a functional block diagram showing an example of a configuration related to a function of the main body portion 12 of the ultrasonography apparatus 13 according to the present embodiment. As shown in FIG. 6, the main body portion 12 comprises a first acquisition unit 80, a difference derivation unit 81, a second acquisition unit 82, a display controller 84, and an imaging controller 90. For example, in the main body portion 12 according to the present embodiment, the processor 30 executes the imaging control program 36 stored in the storage unit 34, so that the processor 30 functions as the first acquisition unit 80, the difference derivation unit 81, the second acquisition unit 82, the display controller 84, and the imaging controller 90.

The imaging controller 90 has a function of outputting the control signal to the transmission/reception circuit 22 of the ultrasound probe 10 as described above in a case of capturing the ultrasound image U. In a case in which the control signal output from the imaging controller 90 is input to the transmission circuit 24 and the reception circuit 26 of the ultrasound probe 10, the sound ray signal is output from the reception circuit 26 of the ultrasound probe 10 to the image generation unit 46 of the main body portion 12 as described above. Under the control of the imaging controller 90, the transmission/reception circuit 22 of the ultrasound probe 10 and the image generation unit 46 of the main body portion 12 continuously acquire the ultrasound image a plurality of times at a fixed frame rate during a capturing period of the ultrasound image.

The first acquisition unit 80 has a function of acquiring the posture information P. As an example, the first acquisition unit 80 according to the present embodiment acquires the posture information P from the detector 14 as described above. As will be described below, the posture information P includes initial posture information P0 imaged by the detector 14 at the start of the imaging and imaging posture information P1 imaged by the detector 14 after the start of the imaging and during the imaging.

The difference derivation unit 81 derives a difference between the initial posture information P0 and the imaging posture information P1. In addition, the difference derivation unit 81 determines whether or not the derived difference is equal to or greater than a threshold value. A method of deriving, via the difference derivation unit 81, a difference between a posture of the palm W1 in the initial posture information P0 and a posture of the palm W1 in the imaging posture information P1, and a method of determining whether or not the difference is equal to or greater than a threshold value are not limited. For example, the difference derivation unit 81 may detect the difference from an outline of the palm W1 in each of the initial posture information P0 and the imaging posture information P1. In this case, the difference derivation unit 81 determines whether or not an amount of change between the outline in the initial posture information P0 and the outline in the imaging posture information P1 is equal to or greater than a threshold value. Examples of the threshold value in this case include a threshold value based on an amount of movement. In addition, specific examples of the threshold value include at least one of a case in which the outline is changed by 20 pixels or more or a case in which positions of three or more fingers are changed regardless of the amount of movement. The difference derivation unit 81 outputs a determination result to the display controller 84.

The second acquisition unit 82 has a function of acquiring the ultrasound image U. As an example, the second acquisition unit 82 according to the present embodiment acquires the ultrasound image U from the storage unit 34. The ultrasound image U acquired by the second acquisition unit 82 is output to the display controller 84.

The display controller 84 has a function of displaying the ultrasound image U on the display unit 44 of the main body portion 12. In addition, the display controller 84 has a function of displaying information representing a warning together with the ultrasound image U in a case in which the determination result input from the difference derivation unit 81 represents that the difference is equal to or greater than the threshold value.

Figure 7:
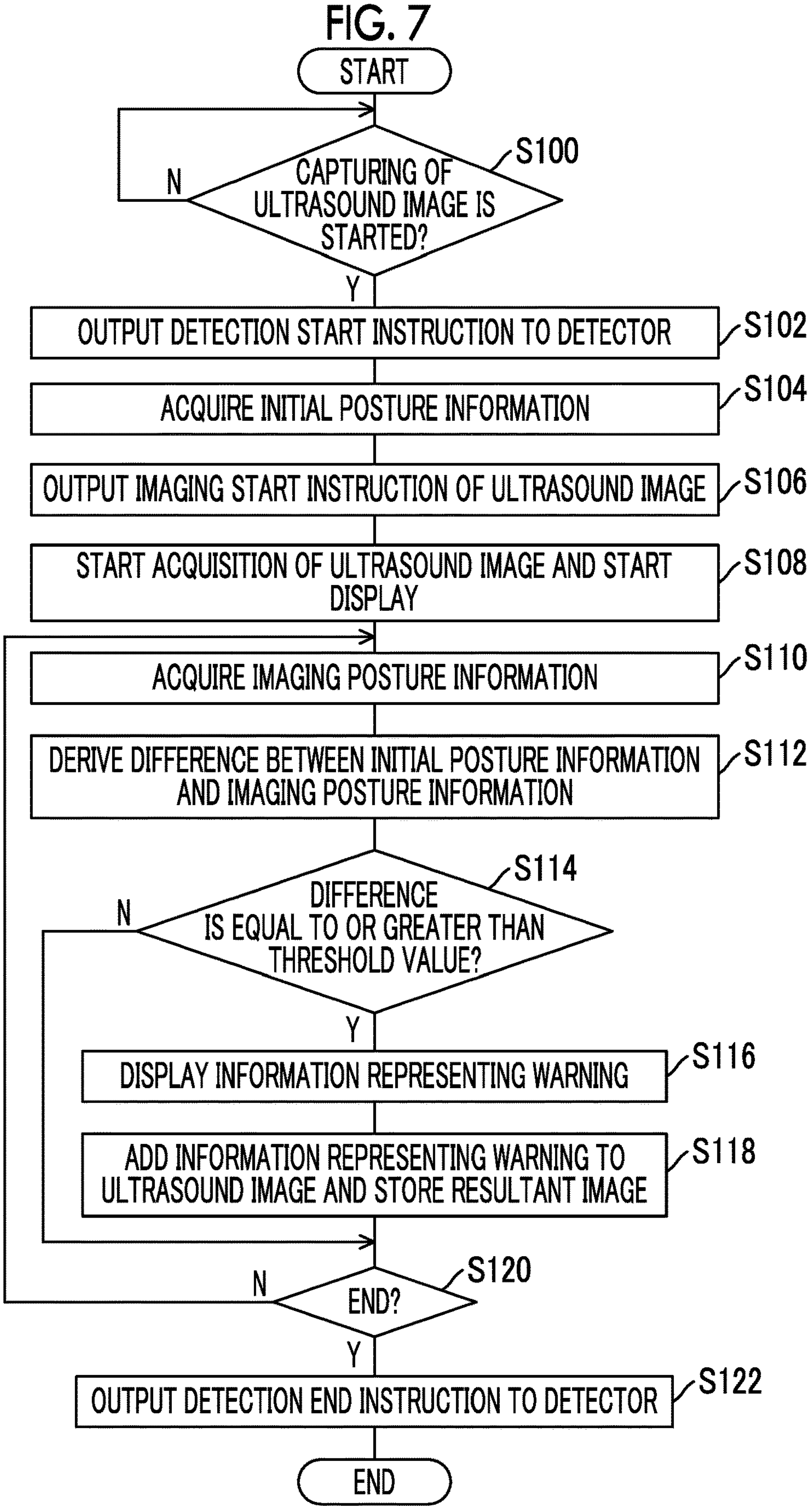
FIG. 7 is a flowchart showing an example of imaging control processing executed by a processor of the main body portion.

Next, an operation of the main body portion 12 according to the present embodiment will be described with reference to the drawings. FIG. 7 shows a flowchart showing an example of a flow of the imaging control processing executed in the main body portion 12 according to the present embodiment. As an example, in the main body portion 12 according to the present embodiment, in a case in which power is supplied to the main body portion 12, the processor 30 executes the imaging control program 36 stored in the storage unit 34 to execute the image processing shown in FIG. 7 as an example.

In step S100 of FIG. 7, the imaging controller 90 determines whether or not to start the capturing of the ultrasound image U. For example, in a case in which an imaging start instruction input by a technician from the input I/F unit 42 is received, the imaging controller 90 determines to start the capturing of the ultrasound image U. In a case in which the capturing of the ultrasound image U is not started, a determination result in step S100 is NO. On the other hand, in a case in which the capturing of the ultrasound image U is started, a determination result in step S100 is YES, and the process proceeds to step S102.

In step S102, the first acquisition unit 80 outputs a start instruction for starting acquisition of the posture information P to the detector 14. As described above, in a case in which the start instruction is input, the detector 14 causes the optical camera to start the imaging of the palm W1 of the subject W at a set frame rate. In addition, the detector 14 estimates the posture information P from the optical camera image of each frame, and outputs the posture information P to the main body portion 12.

In next step S104, the first acquisition unit 80 acquires the initial posture information P0. That is, the posture information P at the start of the capturing of the ultrasound image U is acquired. The main body portion 12 may control the ultrasound probe 10 and the detector 14 such that transmission of an ultrasonic wave or reception of an ultrasound echo corresponding to the first ultrasound image U by the ultrasound probe 10 is synchronized with the imaging of the initial posture information P0 by the optical camera of the detector 14.

In next step S106, the imaging controller 90 outputs the imaging start instruction of the ultrasound image to the ultrasound probe 10. The ultrasound probe 10 outputs an ultrasound beam to the subject W in response to the imaging start instruction, and outputs the obtained sound ray signal to the main body portion 12. As described above, the image generation unit 46 of the main body portion 12 generates the ultrasound image U from the sound ray signal.

In next step S108, the second acquisition unit 82 starts acquisition of the ultrasound image U, and the display controller 84 starts display of the ultrasound image U. After that, until the imaging is ended, the ultrasound image U is captured at a predetermined frame rate, and the generated ultrasound images U are sequentially displayed on the display unit 44.

In next step S110, the second acquisition unit 82 acquires the imaging posture information P1 from the detector 14. That is, the second acquisition unit 82 acquires, as the imaging posture information P1, the posture information P estimated from the optical camera image captured by the optical camera of the detector 14 during the capturing of the ultrasound image U, from the detector 14.

In next step S112, as described above, the difference derivation unit 81 derives the difference between the initial posture information P0 and the imaging posture information P1.

In next step S114, as described above, the difference derivation unit 81 determines whether or not the difference derived by the difference derivation unit 81 is equal to or greater than the threshold value. In a case in which the difference is not equal to or greater than the threshold value, in other words, in a case in which the difference is smaller than the threshold value, a determination result in step S114 is NO, and the process proceeds to step S120.

On the other hand, in a case in which the difference is equal to or greater than the threshold value, a determination result in step S114 is YES, and the process proceeds to step S116. In step S116, as described above, the display controller 84 causes the display unit 44 to display the information representing the warning.

In next step S118, the display controller 84 adds the information representing the warning to the ultrasound image U and stores the resultant image. Specifically, the information representing the warning is added to the ultrasound image U captured at the same timing as a timing at which the imaging posture information P1 used for deriving the difference that is a source of the warning is imaged.

In next step S120, the imaging controller 90 determines whether or not to end the imaging. For example, in a case in which an imaging end instruction input by the technician from the input OF unit 42 is received, the imaging controller 90 determines to end the capturing of the ultrasound image U. In a case in which the imaging is not to be ended, a determination result in step S120 is NO, the process returns to step S110, and the processes of steps S110 to S118 are repeated. On the other hand, in a case in which the imaging is to be ended, a determination result in step S120 is YES, and, in step S122, the imaging controller 90 outputs the end instruction to the detector 14 so that the first acquisition unit 80 ends the acquisition of the posture information P. As described above, in a case in which the end instruction is input, the detector 14 ends the imaging of the palm W1 of the subject W by the optical camera and the estimation of the posture information P from the optical camera image. In a case in which the process in step S122 is ended, the imaging control processing shown in FIG. 7 is ended.

As described above, according to the main body portion 12 according to the present embodiment, in a case in which the posture of the palm W1 of the subject W changes by a threshold value or more from the start of the capturing of the ultrasound image U during the capturing of the ultrasound image U, a warning is displayed. In a case in which the posture of the palm W1 changes by a threshold value or more, a position of a blood vessel in the arm W2 of the subject W may change even though the posture of the arm W2 does not change. In a case in which the position of the blood vessel in the arm W2 changes, a state of the blood vessel B reflected in the ultrasound image U changes. The ultrasound image U in which the state of the blood vessel B has changed in this way may not be preferable for use in diagnosis. For example, in a case in which a series of the ultrasound images U are connected to generate a blood vessel structure image showing a structure of the blood vessel B, the change in the image of the blood vessel B changed from the imaging start may result in noise.

With respect to this, in the present embodiment, as described above, in a case in which the posture of the palm W1 of the subject W changes by the threshold value or more, a warning is displayed, so that the technician who notices the warning tries to return the posture of the palm W1 to the initial state. Accordingly, a state of a blood vessel of the arm W2 of the subject W can be returned to the same state as before the change, that is, at the start of the capturing of the ultrasound image U. Therefore, according to the main body portion 12 according to the present embodiment, it is possible to obtain an ultrasound image suitable for diagnosis.

Next, generation of the blood vessel structure image using a series of the ultrasound images U captured by the ultrasonography apparatus 13 will be described. As an example, in the present embodiment, after a series of the ultrasound images U are captured by the ultrasonography apparatus 13, the blood vessel structure image is generated by an image processing apparatus 18 provided outside the ultrasonography apparatus 13.

Figure 8:
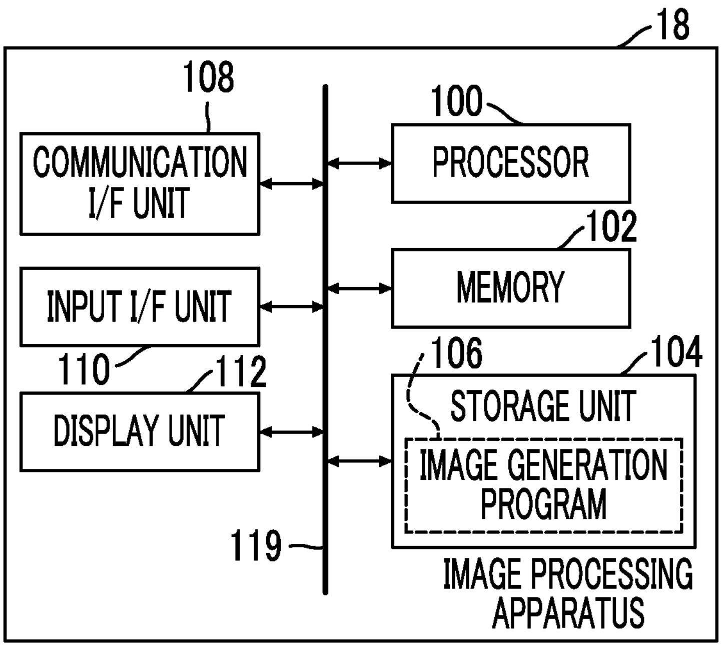
FIG. 8 is a block diagram showing an example of a hardware configuration of an image processing apparatus according to the embodiment.

FIG. 8 shows a configuration diagram showing a hardware configuration of an example of the image processing apparatus 18 according to the present embodiment. As shown in FIG. 8, the image processing apparatus 18 according to the present embodiment comprises a processor 100, a memory 102, a storage unit 104, a communication OF unit 108, an input OF unit 110, and a display unit 112. The processor 100, the memory 102, the storage unit 104, the communication I/F unit 108, the input I/F unit 110, and the display unit 112 are connected to each other via a bus 119 such as a system bus or a control bus such that various kinds of information can be exchanged.

The processor 100 reads out various programs, which include an image generation program 106 stored in the storage unit 104, to the memory 102 and executes processing according to the read-out program. Accordingly, the processor 100 controls the generation of the blood vessel structure image (object-of-interest image). The memory 102 is a work memory that is used for the processor 100 to execute processing.

The storage unit 104 stores the acquired ultrasound image, the image generation program 106, various other kinds of information, and the like. Specific examples of the storage unit 104 include an HDD, an SSD, and an SD card.

The communication I/F unit 108 performs communication of various kinds of information with the main body portion 12 of the ultrasonography apparatus 13 through wireless communication such as WiFi (registered trademark) or Bluetooth (registered trademark) or wired communication.

The input I/F unit 110 and the display unit 112 function as a user interface. The display unit 112 provides the user with various kinds of information regarding the generation of the blood vessel image (object-of-interest image). The display unit 112 is not particularly limited, and examples thereof include a liquid crystal monitor and an LED monitor. In addition, the input I/F unit 110 is operated by the user in order to input various instructions regarding the generation of the blood vessel image (object-of-interest image) and the like. The input I/F unit 110 is not particularly limited, and examples of the input I/F unit 110 include a keyboard, a touch pen, and a mouse. A touch panel display in which the input I/F unit 110 and the display unit 112 are integrated may be adopted.

Figure 9:
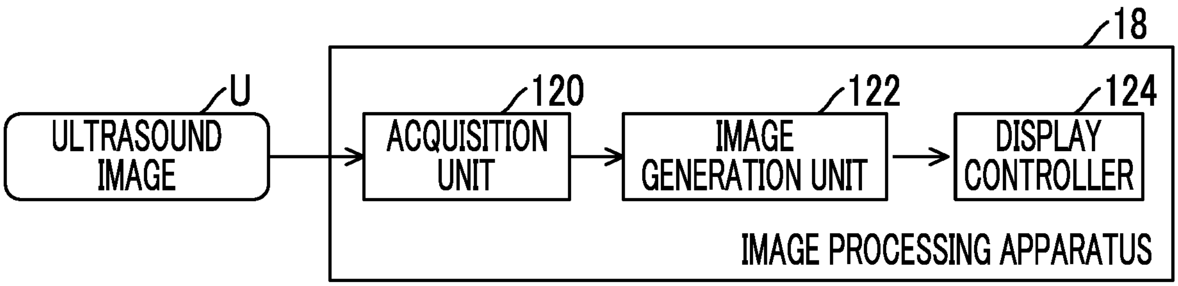
FIG. 9 is a functional block diagram showing an example of a configuration of the image processing apparatus.

Next, a functional configuration of the image processing apparatus 18 will be described. FIG. 9 is a functional block diagram showing an example of a configuration related to a function of the image processing apparatus 18 according to the present embodiment. As shown in FIG. 9, the image processing apparatus 18 comprises an acquisition unit 120, an image generation unit 122, and a display controller 124. For example, in the image processing apparatus 18 according to the present embodiment, the processor 100 executes the image generation program 106 stored in the storage unit 104, so that the processor 100 functions as the acquisition unit 120, the image generation unit 122, and the display controller 124.

The acquisition unit 120 has a function of acquiring an ultrasound image group from the main body portion 12 of the ultrasonography apparatus 13. In a case in which a warning is issued by the imaging control processing of the main body portion 12, the ultrasound images U in a state where information representing the warning is added to the corresponding ultrasound image U are acquired. That is, in a case in which a warning is issued by the imaging control processing of the main body portion 12, the acquisition unit 120 acquires an ultrasound image group including the ultrasound image U to which the warning is added and the ultrasound image U to which the warning is not added. The acquisition unit 120 outputs the acquired ultrasound image group to the image generation unit 122.

The image generation unit 122 generates an object-of-interest image representing an object of interest from each ultrasound image U of the ultrasound image group. In the present embodiment, since a blood vessel is an object of interest, the image generation unit 122 generates a blood vessel structure image showing a structure of the blood vessel B. The blood vessel structure image (object-of-interest image) generated by the image generation unit 122 from the ultrasound image group may be a two-dimensional image configured of pixel data, may be a three-dimensional image configured of voxel data, or may be both the two-dimensional image and the three-dimensional image. A method of generating, via the image generation unit 122, the blood vessel structure image (object-of-interest image) from the ultrasound image group is not particularly limited. A known method can be applied to both a case in which the blood vessel structure image (object-of-interest image) is a two-dimensional image and a case in which the blood vessel structure image (object-of-interest image) is a three-dimensional image. The blood vessel structure image generated by the image generation unit 122 is output to the display controller 124.

The display controller 84 has a function of causing the display unit 112 to display the blood vessel structure image.

Figure 10:
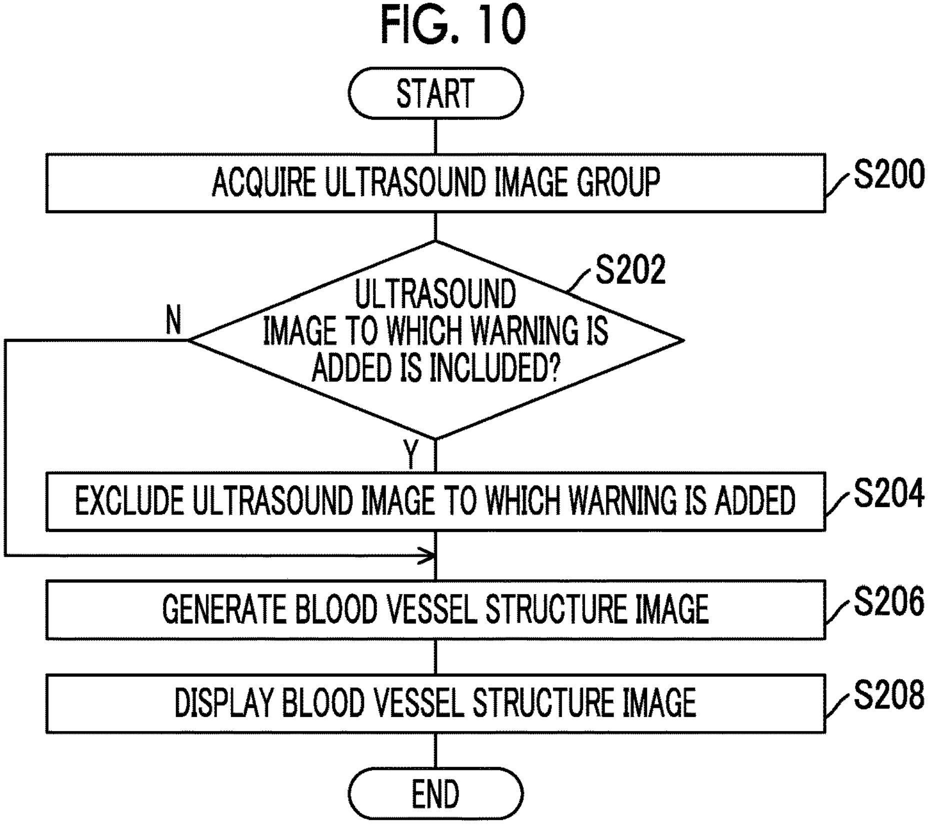
FIG. 10 is a flowchart showing an example of image generation processing executed by a processor of the image processing apparatus.

Next, an action of the image processing apparatus 18 according to the present embodiment will be described with reference to the drawings. FIG. 10 shows a flowchart showing an example of a flow of image generation processing executed in the image processing apparatus 18 according to the present embodiment. As an example, in the main body portion 12 according to the present embodiment, in a case in which the user gives a start instruction for the image generation by the input I/F unit 110, the processor 100 executes the image generation program 106 stored in the storage unit 104 to execute the image generation processing shown in FIG. 10 as an example.

In step S200 of FIG. 10, as described above, the acquisition unit 120 acquires the ultrasound image group including a plurality of the ultrasound images U from the main body portion 12 of the ultrasonography apparatus 13.

In next step S202, the image generation unit 122 determines whether or not the acquired ultrasound image group includes the ultrasound image U to which the warning is added. In a case in which the ultrasound image U to which the warning is added is not included, a determination result in step S202 is NO, and the process proceeds to step S206. On the other hand, in a case in which the ultrasound image U to which the warning is added is included, a determination result in step S202 is YES, and the process proceeds to step S204.

In step S204, the image generation unit 122 excludes the ultrasound image U to which the warning is added, from the ultrasound image group acquired in step S200 described above.

In next step S206, the image generation unit 122 generates the blood vessel structure image from the ultrasound image group as described above. Since, in a case in which the ultrasound image group acquired in step S200 described above includes the ultrasound image U to which the warning is added, the ultrasound image U to which the warning is added is excluded in step S204 described above, the image generation unit 122 generates the blood vessel structure image from the ultrasound image U to which the warning is not added. In this case, for example, the image generation unit 122 may generate a blood vessel structure image in which a portion corresponding to the ultrasound image U to which the warning is added is omitted. In addition, for example, the image generation unit 122 may generate a portion corresponding to the ultrasound image U to which the warning is added, that is, a pseudo ultrasound image corresponding to the excluded ultrasound image U by performing complementation from the ultrasound images U before and after the exclusion, and generate the blood vessel structure image also using the generated pseudo ultrasound image.

In next step S208, the display controller 124 causes the display unit 112 to display the blood vessel structure image generated in step S206 described above. In a case in which the process in step S208 is ended, the image generation processing shown in FIG. 10 is ended.

As described above, according to the image processing shown in FIG. 10, the image generation unit 122 generates the blood vessel structure image without using the ultrasound image U to which the warning is added. Accordingly, the accuracy of the blood vessel structure image can be improved.

Further, a modification example of the image generation processing will be described.

Modification Example 1

Figure 11:
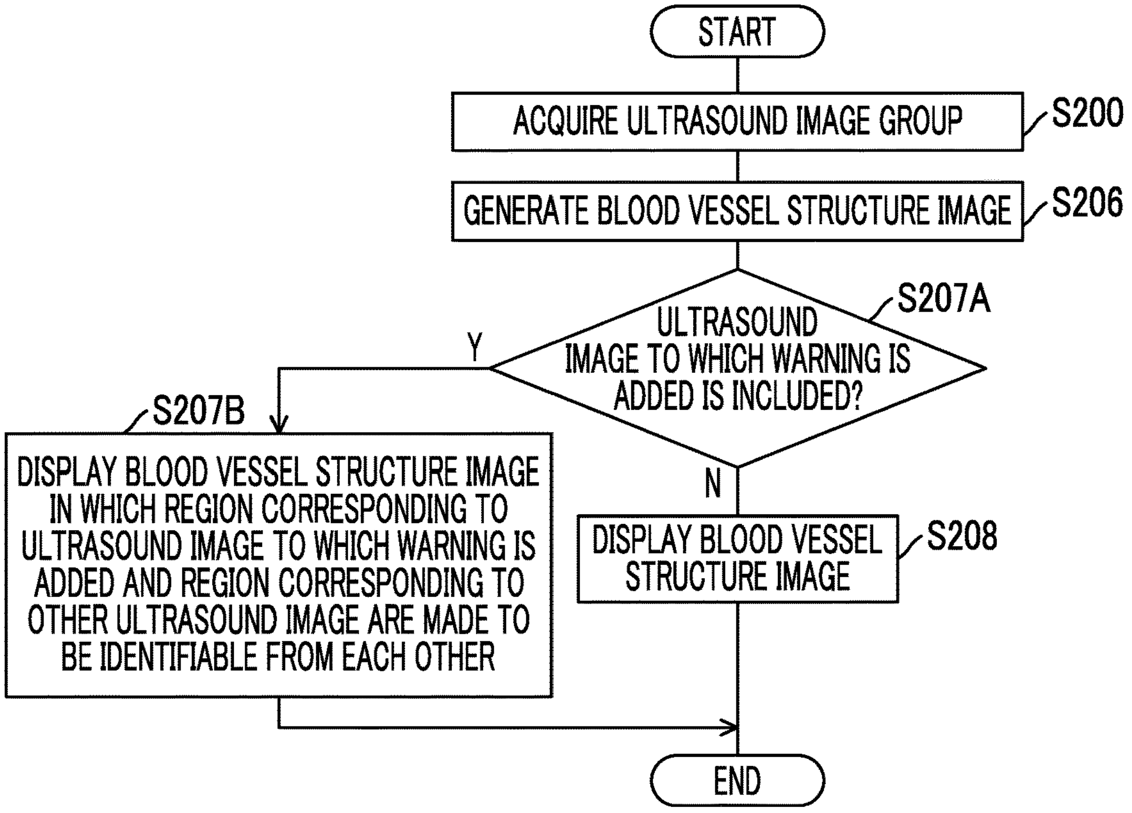
FIG. 11 is a flowchart showing a modification example of the image generation processing executed by the processor of the image processing apparatus.

FIG. 11 shows a flowchart showing an example of a flow of image generation processing executed in the image processing apparatus 18 according to the present modification example. The image generation processing according to the present modification example shown in FIG. 11 is different from the image generation processing shown in FIG. 10 in that the processes of steps S202 and S204 are not provided and after acquiring the ultrasound image group in step S200, the process proceeds to step S206. Therefore, the image generation unit 122 according to the present modification example generates the blood vessel structure image also using the ultrasound image U to which the warning is added. The blood vessel structure image generated in the present modification example is preferably a three-dimensional image.

In addition, the image generation processing according to the present modification example is different from the image generation processing shown in FIG. 10 in that the processes of steps S207A and S207B are included after the process of step S206.

In step S207A in FIG. 11, the image generation unit 122 determines whether or not the ultrasound image group acquired in step S200 described above includes the ultrasound image U to which the warning is added. In a case in which the ultrasound image U to which the warning is added is not included in the ultrasound image group, a determination result in step S207A is NO, and the process proceeds to step S208 described above. On the other hand, in a case in which the ultrasound image U to which the warning is added is included in the ultrasound image group, a determination result in step S207A is YES, and the process proceeds to step S207B.

In step S207B, the display controller 124 causes the display unit 112 to display the blood vessel structure image in which a region generated by the ultrasound image U to which the warning is added and a region generated by the other ultrasound image U, that is, the ultrasound image U to which the warning is not added are made to be identifiable from each other. For example, the display controller 124 displays the blood vessel structure image such that the region generated by the ultrasound image U to which the warning is added is more conspicuous than the region generated by the other ultrasound image U. In addition, for example, the display controller 124 displays the blood vessel structure image by making a color of the region generated by the ultrasound image U to which the warning is added different from a color of the region generated by the other ultrasound image U. In a case in which the process in step S207B is ended, the image processing shown in FIG. 11 is ended.

In this way, by displaying the blood vessel structure image in which the region generated by the ultrasound image U to which the warning is added and the region generated by the other ultrasound image U are made to be identifiable from each other, the user can visually recognize a region where the accuracy of generation may have decreased.

Modification Example 2

The blood vessel structure image generated in the present modification example is preferably a three-dimensional image as in Modification Example 1.

Figure 12:
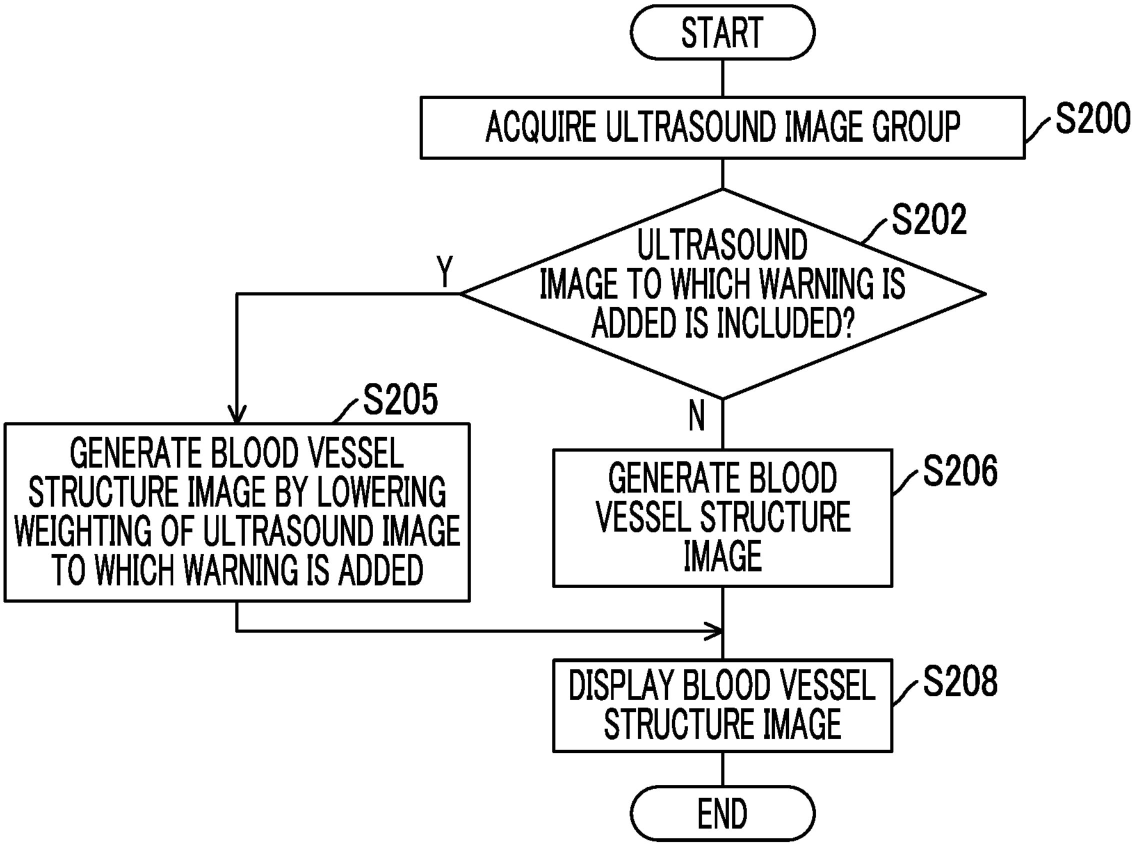
FIG. 12 is a flowchart showing a modification example of the image generation processing executed by the processor of the image processing apparatus.

FIG. 12 shows a flowchart showing an example of a flow of image generation processing executed in the image processing apparatus 18 according to the present modification example. The image generation processing according to the present modification example shown in FIG. 12 is different from the image generation processing shown in FIG. 10 in that the process of step S204 is not provided and in a case in which a determination result in step S202 is NO, that is, in a case in which the ultrasound image U to which the warning is added is not included in the ultrasound image group, the process proceeds to step S206.

In addition, the image generation processing according to the present modification example is different from the image generation processing shown in FIG. 10 in that in a case in which a determination result in step S202 is YES, the process proceeds to step S205.

In step S205 of FIG. 12, the image generation unit 122 generates the blood vessel structure image by making a weighting of the ultrasound image U to which the warning is added relatively lower than that of the ultrasound image U to which the warning is not added. For example, the image generation unit 122 may make the weighting of the ultrasound image U to which the warning is added relatively lower than that of the ultrasound image U to which the warning is not added, at a boundary portion between the ultrasound image U to which the warning is added and the ultrasound image U to which the warning is not added. In addition, for example, the image generation unit 122 may make the weighting of the ultrasound image U to which the warning is added relatively lower than that of the ultrasound image U to which the warning is not added, in the whole ultrasound image U to which the warning is added. In a case in which the process in step S205 is ended, the process proceeds to step S208.

In this way, in a case in which the blood vessel structure image is generated by making the weighting of the ultrasound image U to which the warning is added lower than that of the ultrasound image U to which the warning is not added, it is possible to suppress the decrease in accuracy of the blood vessel structure image by generating the blood vessel structure image using the ultrasound image U to which the warning is added.

As described above, according to the image processing apparatus 18 according to the present embodiment, it is possible to obtain a region-of-interest image (blood vessel structure image) suitable for a diagnosis.

The technique of the present disclosure is not limited to each of the above-described embodiments, and various modifications can be made.

For example, the detector 14 that detects the posture information P is not limited to the above-described form. For example, the detector 14 may be a detector 14 that estimates the posture information P from a sensor value output from a sensor as with the detector 14 that estimates the posture information P from the optical camera image captured by the optical camera described above. In addition, for example, the detector 14 may be a detector that uses the sensor value itself output from the sensor as the posture information P. That is, whether or not the detector 14 needs to estimate the posture information P is different depending on the used sensor.

Specifically, the detector 14 may be, for example, a combination of a tracking marker worn on a finger of the subject W and an optical camera. In addition, the detector 14 may be capable of detecting any one of a finger spacing, a finger angle, or a three-dimensional structure of a skeleton of the finger of the subject W. For example, the detector 14 may be a ring type sensor that is worn on the finger of the subject W or an electrostatic sensor that is worn on the palm W1 and that detects a change in static electricity. In addition, for example, the detector 14 may be a magnetic sensor that detects a change in magnetism. In addition, for example, the detector 14 may be a pressure sensor that detects a contact state of the finger or the palm W1. In addition, for example, the detector 14 may be a conductive glove worn on the palm W1 of the subject W.

In addition, for example, the detector 14 may be a distance measurement device using a laser, visible light, or the like. As the distance measurement device, light detection and ranging (LiDAR) that is a distance-measuring sensor which transmits a detection wave (laser) to the palm W1 of the subject W and receives a reflected wave from the palm W1 to measure a detection distance to the palm W1 may be used. In addition, as the distance measurement device, a camera that comprises a depth sensor and obtains an image configured of pixels having distance information to the palm W1, or a depth camera that comprises two optical cameras and can measure a distance from the parallax to the palm W1 may be used. In addition, as the distance measurement device, a communication device using WiFi (registered trademark), which is a general-purpose communication device having a wave transmitting part with a center frequency of 2.4/5 GHz and a wave receiving part with a plurality of receiving channels such as a bandwidth of 20/40/80/160 MHz, may be used. In addition, as the distance measurement device, a radar device using a frequency-modulated continuous wave and having a wave transmitting part that transmits a wideband (1.78 GHz) signal and a wave receiving part comprising a T-type antenna array may be used. In a case in which the distance measurement device uses LiDAR, WiFi, or a radar, the posture information P can be restored by analyzing the reflected wave with a deep learning model. In addition, in a case in which the distance measurement device uses a LiDAR comprising a camera or a depth camera, a position of a joint of the subject W can be grasped by image processing, and a distance from the camera at the corresponding pixel can be measured, so that the posture information P can be obtained.

In the above description, an aspect in which, in the imaging control processing for capturing the ultrasound image U, the main body portion 12 of the ultrasonography apparatus 13 performs a control of synchronizing the timing at which the capturing of the ultrasound image U is started with the timing at which the posture information P is acquired by the detector 14 has been described. However, the method of synchronizing both timings is not limited to the present aspect. For example, an aspect may be used in which each of the main body portion 12 or the ultrasound probe 10 and the detector 14 comprises a timepiece with the same time point, and starts the capturing of the ultrasound image U and starts the detection of the posture information P at a timing when each timepiece indicates a set time point.

In addition, for example, in capturing the ultrasound image U of the subject W, pre-capturing of the ultrasound image U may be performed while changing the posture of the palm W1, and, in a case in which the image of the blood vessel B in the ultrasound image U is in a preferable state, for example, in a case in which the image has a preferable shape, the subject W may be instructed, to maintain the posture of the palm W1 in that state.

In addition, in the above-described aspect, for example, as a hardware structure of a processing unit that executes various types of processing such as the first acquisition unit 80, the difference derivation unit 81, the second acquisition unit 82, the display controller 84, and the imaging controller 90, or such as the acquisition unit 120, the image generation unit 122, and the display controller 124, various processors shown below can be used. As described above, the various processors include, in addition to a central processing unit (CPU) which is a general-purpose processor that executes software (program) to function as various processing units, a programmable logic device (PLD) which is a processor whose circuit configuration can be changed after manufacturing such as a field programmable gate array (FPGA), and a dedicated circuitry which is a processor having a circuit configuration specifically designed to execute specific processing such as an application specific integrated circuit (ASIC).

One processing unit may be configured of one of the various processors, or configured of a combination of the same or different kinds of two or more processors (for example, a combination of a plurality of FPGAs or a combination of the CPU and the FPGA). In addition, a plurality of processing units may be configured of one processor.

As an example of configuring a plurality of processing units with one processor, first, there is a form in which, as typified by computers such as a client and a server, one processor is configured by combining one or more CPUs and software, and the processor functions as a plurality of processing units. Second, there is a form in which, as typified by a system on chip (SoC) and the like, in which a processor that implements functions of an entire system including a plurality of processing units with one integrated circuit (IC) chip is used. As described above, the various processing units are configured by using one or more of the various processors described above as a hardware structure.

Further, as the hardware structure of these various processors, more specifically, an electric circuit (circuitry) in which circuit elements such as semiconductor elements are combined can be used.

In addition, in each of the above-described embodiments, an aspect in which the imaging control program 36 is stored (installed) in the storage unit 34 in advance, and the image generation program 106 is stored (installed) in the storage unit 104 in advance has been described, but the present invention is not limited to this. Each of the imaging control program 36 and the image generation program 106 may be provided in a form recorded in a recording medium such as a compact disc read only memory (CD-ROM), a digital versatile disc read only memory (DVD-ROM), and a universal serial bus (USB) memory. In addition, each of the imaging control program 36 and the image generation program 106 may be downloaded from an external device via a network.

From the above description, the invention described in Appendices described below can be grasped.

Appendix 1

An ultrasonography apparatus comprising: at least one processor, in which the processor acquires, from a detector that detects a posture of a palm of a subject in capturing an ultrasound image, information representing a posture of the palm at a first time point as a first detection result, acquires information representing a posture of the palm at a second time point, which is after the first time point and is a time point during capturing of the ultrasound image, as a second detection result, derives a difference between the posture of the palm at the first time point and the posture of the palm at the second time point based on the first detection result and the second detection result, and performs notification in a case in which the derived difference is equal to or greater than a threshold value.

Appendix 2

The ultrasonography apparatus according to Appendix 1, in which the first time point is a start time point of capturing the ultrasound image.

Appendix 3

The ultrasonography apparatus according to Appendix 1 or 2, in which the processor adds information representing a warning to the ultrasound image captured at the second time point in a case in which the derived difference is equal to or greater than the threshold value.

Appendix 4

An image processing apparatus performing image processing on a plurality of ultrasound images captured by an ultrasonography apparatus that acquires, from a detector that detects a posture of a palm of a subject in capturing an ultrasound image, information representing a posture of the palm at a first time point as a first detection result, acquires information representing a posture of the palm at a second time point, which is after the first time point and is a time point during capturing of the ultrasound image, as a second detection result, derives a difference between the posture of the palm at the first time point and the posture of the palm at the second time point based on the first detection result and the second detection result, and adds information representing a warning to the ultrasound image captured at the second time point in a case in which the derived difference is equal to or greater than a threshold value, the image processing apparatus comprising: at least one processor, in which the processor acquires the plurality of ultrasound images captured by the ultrasonography apparatus, and generates an object-of-interest image from the plurality of ultrasound images.

Appendix 5

The image processing apparatus according to Appendix 4, in which, in a case in which the acquired plurality of the ultrasound images include the ultrasound image to which the information representing the warning is added, the processor generates the object-of-interest image from the plurality of ultrasound images excluding the ultrasound image to which the information representing the warning is added.

Appendix 6

The image processing apparatus according to Appendix 4, in which the processor displays a region generated from the ultrasound image to which the information representing the warning is added and a region generated from an ultrasound image other than the ultrasound image to which the information representing the warning is added, of the generated object-of-interest image, in an identifiable manner.

Appendix 7

The image processing apparatus according to Appendix 4, in which the processor generates the object-of-interest image by making a weighting of the ultrasound image to which the information representing the warning is added different from a weighting of an ultrasound image other than the ultrasound image to which the information representing the warning is added.

Appendix 8

The image processing apparatus according to any one of Appendices 4 to 7, in which the ultrasound image is at least one of a two-dimensional image or a three-dimensional image.

Appendix 9

An ultrasound image capturing method executed by a processor, the method comprising: acquiring, from a detector that detects a posture of a palm of a subject in capturing an ultrasound image, information representing a posture of the palm at a first time point as a first detection result; acquiring information representing a posture of the palm at a second time point, which is after the first time point and is a time point during capturing of the ultrasound image, as a second detection result; deriving a difference between the posture of the palm at the first time point and the posture of the palm at the second time point based on the first detection result and the second detection result; and performing notification in a case in which the derived difference is equal to or greater than a threshold value.

Appendix 10

An ultrasound image capturing program for causing a processor to execute a process comprising: acquiring, from a detector that detects a posture of a palm of a subject in capturing an ultrasound image, information representing a posture of the palm at a first time point as a first detection result; acquiring information representing a posture of the palm at a second time point, which is after the first time point and is a time point during capturing of the ultrasound image, as a second detection result; deriving a difference between the posture of the palm at the first time point and the posture of the palm at the second time point based on the first detection result and the second detection result; and performing notification in a case in which the derived difference is equal to or greater than a threshold value.

What is claimed is:

1. An ultrasonography apparatus comprising:
- an ultrasound probe; and
- at least one processor,
- wherein the processor:
  - controls the ultrasound probe and an optical camera in a time-synchronous manner such that:
    - a first ultrasound image of a first portion of a subject is acquired by the ultrasound probe at a first time point and a second ultrasound image of the first portion of the subject is acquired by the ultrasound probe at a second time point, which is after the first time point, the first portion of the subject including a portion of an arm of the subject, and
    - optical images of a second portion of the subject are acquired by the optical camera, the second portion of the subject including a palm of the subject, such that information representing a posture of the palm at the first time point is detected as a first detection result, and information representing a posture of the palm at the second time point is detected as a second detection result,
  - derives a difference between the posture of the palm at the first time point and the posture of the palm at the second time point based on the first detection result and the second detection result, and
  - notifies a warning and adds information representing the warning to the second ultrasound image in a case in which the derived difference is equal to or greater than a threshold value.

2. The ultrasonography apparatus according to claim 1, wherein the first time point is a start time point of acquiring a plurality of ultrasound images including the first ultrasound image and the second ultrasound image.

3. An image processing apparatus performing image processing on a plurality of ultrasound images acquired by an ultrasonography apparatus that includes an ultrasound probe, the ultrasonography apparatus controlling the ultrasound probe and an optical camera in a time-synchronous manner such that a first ultrasound image of a first portion of a subject is acquired by the ultrasound probe at a first time point and a second ultrasound image of the first portion of the subject is acquired by the ultrasound probe at a second time point, which is after the first time point, the first portion of the subject including a portion of an arm of the subject, and optical images of a second portion of the subject are acquired by the optical camera, the second portion of the subject including a palm of the subject, such that information representing a posture of the palm at the first time point is detected as a first detection result, and information representing a posture of the palm at the second time point is detected as a second detection result, deriving a difference between the posture of the palm at the first time point and the posture of the palm at the second time point based on the first detection result and the second detection result, and notifying a warning and adding information representing the warning to the second ultrasound image in a case in which the derived difference is equal to or greater than a threshold value, the image processing apparatus comprising:

at least one processor, wherein the processor acquires the plurality of ultrasound images acquired by the ultrasonography apparatus, and generates an object-of-interest image from the plurality of ultrasound images.

4. The image processing apparatus according to claim 3, wherein, in a case in which the acquired plurality of the ultrasound images include the second ultrasound image to which the information representing the warning is added, the processor generates the object-of-interest image from the plurality of ultrasound images excluding the second ultrasound image to which the information representing the warning is added.

5. The image processing apparatus according to claim 3, wherein the processor displays a region generated from the second ultrasound image to which the information representing the warning is added and a region generated from a third ultrasound image other than the second ultrasound image to which the information representing the warning is added, of the generated object-of-interest image, in an identifiable manner.

6. The image processing apparatus according to claim 3, wherein the processor generates the object-of-interest image by making a weighting of the second ultrasound image to which the information representing the warning is added different from a weighting of a third ultrasound image other than the second ultrasound image to which the information representing the warning is added.

7. An ultrasound image acquiring method executed by a processor, the method comprising:

controlling an ultrasound probe and an optical camera in a time-synchronous manner such that:

a first ultrasound image of a first portion of a subject is acquired by the ultrasound probe at a first time point and a second ultrasound image of the first portion of the subject is acquired by the ultrasound probe at a second time point, which is after the first time point, the first portion of the subject including a portion of an arm of the subject, and optical images of a second portion of the subject are acquired by the optical camera, the second portion of the subject including a palm of the subject, such that information representing a posture of the palm at the first time point is detected as a first detection result, and information representing a posture of the palm at the second time point is detected as a second detection result;

deriving a difference between the posture of the palm at the first time point and the posture of the palm at the second time point based on the first detection result and the second detection result; and notifying a warning and adding information representing the warning to the second ultrasound image in a case in which the derived difference is equal to or greater than a threshold value.

8. A non-transitory computer-readable storage medium storing an ultrasound image acquiring program for causing a processor to execute a process comprising:

controlling an ultrasound probe and an optical camera in a time-synchronous manner such that:

a first ultrasound image of a first portion of a subject is acquired by the ultrasound probe at a first time point and a second ultrasound image of the first portion of the subject is acquired by the ultrasound probe at a second time point, which is after the first time point, the first portion of the subject including a portion of an arm of the subject, and optical images of a second portion of the subject are acquired by the optical camera, the second portion of the subject including a palm of the subject, such that information representing a posture of the palm at the first time point is detected as a first detection result, and information representing a posture of the palm at the second time point is detected as a second detection result;

deriving a difference between the posture of the palm at the first time point and the posture of the palm at the second time point based on the first detection result and the second detection result; and notifying a warning and adding information representing the warning to the second ultrasound image in a case in which the derived difference is equal to or greater than a threshold value.

* * * * *